(12) United States Patent
Hu (10) Patent No.: US 8,309,090 B2
(45) Date of Patent: Nov. 13, 2012

(54) MONOCLONAL ANTIBODIES FOR NEUTRALIZING ANTHRAX TOXIN

(75) Inventor: Wei-Gang Hu, Medicine Hat (CA)

(73) Assignee: Her Majesty the Queen in Right of Canada as Represented by the Minister of National Defense, Ottawa (CA)

( * ) Notice: Subject to any disclaimer, the term of this patent is extended or adjusted under 35 U.S.C. 154(b) by 386 days.

(21) Appl. No.: 12/553,766

(22) Filed: Sep. 3, 2009

(65) Prior Publication Data

US 2010/0111868 A1    May 6, 2010

Related U.S. Application Data

(60) Provisional application No. 61/094,775, filed on Sep. 5, 2008.

(51) Int. Cl.
*A61K 39/40*  (2006.01)
*C07K 16/00*  (2006.01)
*C12N 5/07*   (2010.01)
*C12N 5/00*   (2006.01)

(52) U.S. Cl. ............... 424/150.1; 424/164.1; 530/388.4; 435/332; 435/346; 435/354

(58) Field of Classification Search ........................ None
See application file for complete search history.

(56) References Cited

U.S. PATENT DOCUMENTS 7,456,264 B2   11/2008   Keler et al.

FOREIGN PATENT DOCUMENTS

| WO | WO/2005/023177 | 3/2005 |
| WO | WO/2007/084107 | 7/2007 |

OTHER PUBLICATIONS

Rader et al. PNAS, 95:8910-8915, 1998.*
Mohamed, N. et al. Enhancement of Anthrax Lethal Toxin Cytotoxicity: a Subset of Monoclonal Antibodies Against Protective Antigen Increases Lethal Toxin-Mediated Killing of Murine Macrophages. 2004. Infec. and Imm. 72: 3276-3283.
Sawada-Hirai et al. Human Anti-Anthrax Protective Antigen Neutralizing Monoclonal Antibodies Derived from Donors Vaccinated with Anthrax Vaccine Adsorbed. 2004 Journal of Immune Based Therapies and Vaccines. 2:1-15.
European Search Report issued in EP 09 16 9535 filed on Sep. 4, 2009.
F. Brossier et al.: "Functional analysis of *Bacillus anthracis* protective antigen by using neutralizing monoclonal antibodies." Infection and Immunity, vol. 72, No. 11, Nov. 2004, pp. 6313-6317.
M. Gubbins et al.: "Production and characterization of neutralizing monoclonal antibodies that recognize an epitope in domain 2 of *Bacillus anthracis* protective antigen." FEMS Immunology and Medical Microbiology, vol. 47, No. 3, Aug. 2006, pp. 436-443.
S. Little et al.: "Production and characterization of monoclonal antibodies to the protective antigen component of *Bacillus anthracis* toxin." Infection and Immunity, vol. 56, No. 7, Jul. 1988, pp. 1807-1813.
J. Rivera et al.: "A monoclonal antibody to *Bacillus antracis* protective antigen defines a neutralizing epitope in domain 1." Infection and Immunity, vol. 74, No. 7, Jul. 2006, pp. 4149-4156.
W-G. Hu et al.: "A novel approach to development of monoclonal antibodies using native antigen for immunization and recombinant antigen for screening." Hybridoma, vol. 27, No. 4, Aug. 2008, pp. 307-311.
B. Zhou et al.: "Selection and characterization of human antibodies neutralizing *Bacillus anthracis* toxin." Bioorganic & Medicinal Chemistry, vol. 15, No. 4, Nov. 5, 2007, pp. 1903-1913.

* cited by examiner

*Primary Examiner* — S. Devi
(74) *Attorney, Agent, or Firm* — Santosh K. Chari; Blake, Cassels & Graydon LLP

(57) ABSTRACT

Isolated monoclonal antibodies that bind and/or neutralize anthrax protective antigen (PA) are disclosed as well as hybridomas secreting such antibodies. The invention also provides anti-PA fragments of the antibodies of the invention and recombinantly produced antibodies. Also provided are pharmaceutical compositions containing the antibodies or antibody fragments and uses and methods involving same.

8 Claims, 2 Drawing Sheets

SEQUENCE LISTING

```
<160> NUMBER OF SEQ ID NOS: 20

<210> SEQ ID NO 1
<211> LENGTH: 354
<212> TYPE: DNA
<213> ORGANISM: mouse

<400> SEQUENCE: 1
caggtcaagc tgcaggagtc tggagctgag ctggtgaggc ctggggcttc agtgaagctg      60
tcctgcaaga cttctggata catcttcacc aactactgga ttcactgggt aaaacagagg     120
tctggacagg gccttgagcg gattgcaagg atttatcctg gaactggtgg tacttactac     180
aatgagaagt tcaagggcaa ggccacactg actgcagaca aatcctccag cactgcctac     240
atgcagctca gcagcctgaa atctgaggac tctgctgtct atttctgtgc aagatgggat     300
ctacatttct ctatggacta ctggggccaa gggaccacgg tcaccgtctc ctca           354

<210> SEQ ID NO 2
<211> LENGTH: 118
<212> TYPE: PRT
<213> ORGANISM: mouse

<400> SEQUENCE: 2

Gln Val Lys Leu Gln Glu Ser Gly Ala Glu Leu Val Arg Pro Gly Ala
1               5                   10                  15

Ser Val Lys Leu Ser Cys Lys Thr Ser Gly Tyr Ile Phe Thr Asn Tyr
            20                  25                  30

Trp Ile His Trp Val Lys Gln Arg Ser Gly Gln Gly Leu Glu Arg Ile
        35                  40                  45
```

```
Ala Arg Ile Tyr Pro Gly Thr Gly Gly Thr Tyr Tyr Asn Glu Lys Phe
        50                  55                  60

Lys Gly Lys Ala Thr Leu Thr Ala Asp Lys Ser Ser Thr Ala Tyr
65                  70                  75                  80

Met Gln Leu Ser Ser Leu Lys Ser Glu Asp Ser Ala Val Tyr Phe Cys
                85                  90                  95

Ala Arg Trp Asp Leu His Phe Ser Met Asp Tyr Trp Gly Gln Gly Thr
            100                 105                 110

Thr Val Thr Val Ser Ser
            115

<210> SEQ ID NO 3
<211> LENGTH: 321
<212> TYPE: DNA
<213> ORGANISM: mouse

<400> SEQUENCE: 3
caaattgttc tcacccagtc tccagcaatc atgtctgcat ctccagggga gaaggtcacc      60
atgacctgca gtgccagttc aagtgtacgt tacatgcact ggtaccagca gaagtcgggc     120
acctccccca aaagatggat ttatgacaca tccaaactgg cttctggagt ccctgctcgc     180
ttcagtggca gtgggtctgg gacctcttac tctctcacaa tcagcagcat ggaggctgaa     240
gatgctgcca cttattactg ccagcagtgg agtggtaacc cgctcacgtt cggtgctggg     300
accaagctgg aaataaaacg g                                               321

<210> SEQ ID NO 4
<211> LENGTH: 107
<212> TYPE: PRT
<213> ORGANISM: mouse

<400> SEQUENCE: 4

Gln Ile Val Leu Thr Gln Ser Pro Ala Ile Met Ser Ala Ser Pro Gly
1               5                   10                  15

Glu Lys Val Thr Met Thr Cys Ser Ala Ser Ser Ser Val Arg Tyr Met
                20                  25                  30

His Trp Tyr Gln Gln Lys Ser Gly Thr Ser Pro Lys Arg Trp Ile Tyr
            35                  40                  45

Asp Thr Ser Lys Leu Ala Ser Gly Val Pro Ala Arg Phe Ser Gly Ser
        50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Ser Gly Asn Pro Leu Thr
                85                  90                  95

Phe Gly Ala Gly Thr Lys Leu Glu Ile Lys Arg
            100                 105

<210> SEQ ID NO 5
<211> LENGTH: 345
<212> TYPE: DNA
<213> ORGANISM: mouse

<400> SEQUENCE: 5
gaggtgaagc tgcaggagtc wggaggaggc ttggtgcaac ctggaggatc catgaaactc      60
tcttgtgctg cctctggatt cagttttagt gacgcctgga tggactgggt ccgccagtct     120
ccagagaagg ggcttgagtg ggttgctgaa attagaagca aagctaagaa tcatgcaaca     180
ttctatgctg agtctgtgaa agggaggttc accatctcaa gagatgattc caaaagtagt     240
```

```
gtctacctgc aaatgaacag cttaagaggt gaagacactg gcatttatta ctgcaccgct    300
gggacgggcg tctggggcca agggaccacg gtcaccgtct cctca                   345
```

<210> SEQ ID NO 6
<211> LENGTH: 115
<212> TYPE: PRT
<213> ORGANISM: mouse

<400> SEQUENCE: 6

```
Glu Val Lys Leu Gln Glu Ser Gly Gly Gly Leu Val Gln Pro Gly Gly
1               5                   10                  15

Ser Met Lys Leu Ser Cys Ala Ala Ser Gly Phe Ser Phe Ser Asp Ala
                20                  25                  30

Trp Met Asp Trp Val Arg Gln Ser Pro Glu Lys Gly Leu Glu Trp Val
            35                  40                  45

Ala Glu Ile Arg Ser Lys Ala Lys Asn His Ala Thr Phe Tyr Ala Glu
        50                  55                  60

Ser Val Lys Gly Arg Phe Thr Ile Ser Arg Asp Asp Ser Lys Ser Ser
65                  70                  75                  80

Val Tyr Leu Gln Met Asn Ser Leu Arg Gly Glu Asp Thr Gly Ile Tyr
                85                  90                  95

Tyr Cys Thr Ala Gly Thr Gly Val Trp Gly Gln Gly Thr Thr Val Thr
                100                 105                 110

Val Ser Ser
        115
```

<210> SEQ ID NO 7
<211> LENGTH: 339
<212> TYPE: DNA
<213> ORGANISM: mouse

<400> SEQUENCE: 7

```
gacatccaga tgacvcagtc tccactcact ttgtcggtta cctttggaca accagcctcc    60
atctcttgca agtcaagtca gagcctctta gctagtgatg gagagacata tttgaattgg   120
ttgttacaga ggccagacca gtctctaaag cgcctaatct atctggtgtc taaactggac   180
tctggagtcc ctgacaggtt cactggcagt ggatcaggga cagatttcac actgaaaatc   240
agcagagtgg aggctgagga tttgggagtt tattattgtt ggcaaggtac acattttcct   300
cagacgttcg gtggaggcac cgagctggaa ttcaaacgg                          339
```

<210> SEQ ID NO 8
<211> LENGTH: 113
<212> TYPE: PRT
<213> ORGANISM: mouse

<400> SEQUENCE: 8

```
Asp Ile Gln Met Thr Gln Ser Pro Leu Thr Leu Ser Val Thr Phe Gly
1               5                   10                  15

Gln Pro Ala Ser Ile Ser Cys Lys Ser Ser Gln Ser Leu Leu Ala Ser
                20                  25                  30

Asp Gly Glu Thr Tyr Leu Asn Trp Leu Leu Gln Arg Pro Asp Gln Ser
            35                  40                  45

Leu Lys Arg Leu Ile Tyr Leu Val Ser Lys Leu Asp Ser Gly Val Pro
        50                  55                  60

Asp Arg Phe Thr Gly Ser Gly Ser Gly Thr Asp Phe Thr Leu Lys Ile
65                  70                  75                  80

Ser Arg Val Glu Ala Glu Asp Leu Gly Val Tyr Tyr Cys Trp Gln Gly
```

```
                        85                  90                  95
Thr His Phe Pro Gln Thr Phe Gly Gly Gly Thr Glu Leu Glu Phe Lys
                100                 105                 110
Arg

<210> SEQ ID NO 9
<211> LENGTH: 5
<212> TYPE: PRT
<213> ORGANISM: mouse

<400> SEQUENCE: 9

Asn Tyr Trp Ile His
1               5

<210> SEQ ID NO 10
<211> LENGTH: 17
<212> TYPE: PRT
<213> ORGANISM: mouse

<400> SEQUENCE: 10

Arg Ile Tyr Pro Gly Thr Gly Gly Thr Tyr Tyr Asn Glu Lys Phe Lys
1               5                   10                  15

Gly

<210> SEQ ID NO 11
<211> LENGTH: 9
<212> TYPE: PRT
<213> ORGANISM: mouse

<400> SEQUENCE: 11

Trp Asp Leu His Phe Ser Met Asp Tyr
1               5

<210> SEQ ID NO 12
<211> LENGTH: 10
<212> TYPE: PRT
<213> ORGANISM: mouse

<400> SEQUENCE: 12

Ser Ala Ser Ser Ser Val Arg Tyr Met His
1               5                   10

<210> SEQ ID NO 13
<211> LENGTH: 7
<212> TYPE: PRT
<213> ORGANISM: mouse

<400> SEQUENCE: 13

Asp Thr Ser Lys Leu Ala Ser
1               5

<210> SEQ ID NO 14
<211> LENGTH: 9
<212> TYPE: PRT
<213> ORGANISM: mouse

<400> SEQUENCE: 14

Gln Gln Trp Ser Gly Asn Pro Leu Thr
1               5

<210> SEQ ID NO 15
<211> LENGTH: 5
<212> TYPE: PRT
<213> ORGANISM: mouse
```

```
<400> SEQUENCE: 15

Asp Ala Trp Met Asp
1               5

<210> SEQ ID NO 16
<211> LENGTH: 19
<212> TYPE: PRT
<213> ORGANISM: mouse

<400> SEQUENCE: 16

Glu Ile Arg Ser Lys Ala Lys Asn His Ala Thr Phe Tyr Ala Glu Ser
1               5                   10                  15

Val Lys Gly

<210> SEQ ID NO 17
<211> LENGTH: 4
<212> TYPE: PRT
<213> ORGANISM: mouse

<400> SEQUENCE: 17

Gly Thr Gly Val
1

<210> SEQ ID NO 18
<211> LENGTH: 16
<212> TYPE: PRT
<213> ORGANISM: mouse

<400> SEQUENCE: 18

Lys Ser Ser Gln Ser Leu Leu Ala Ser Asp Gly Glu Thr Tyr Leu Asn
1               5                   10                  15

<210> SEQ ID NO 19
<211> LENGTH: 7
<212> TYPE: PRT
<213> ORGANISM: mouse

<400> SEQUENCE: 19

Leu Val Ser Lys Leu Asp Ser
1               5

<210> SEQ ID NO 20
<211> LENGTH: 9
<212> TYPE: PRT
<213> ORGANISM: mouse

<400> SEQUENCE: 20

Trp Gln Gly Thr His Phe Pro Gln Thr
1               5
```

MONOCLONAL ANTIBODIES FOR NEUTRALIZING ANTHRAX TOXIN

CROSS REFERENCE TO PRIOR APPLICATIONS

The present claims priority from U.S. application No. 61/094,775, filed Sep. 5, 2008, the entire contents of which are incorporated herein by reference.

FIELD OF THE INVENTION

The present invention relates to antibodies that bind or neutralize anthrax toxin. In particular, the invention provides monoclonal antibodies that neutralize anthrax protective antigen (PA).

DESCRIPTION OF THE PRIOR ART

*Bacillus anthracis*, the cause of anthrax, is classified as a category A (most dangerous) biological bioterrorism (BT) and biowarfare (BW) agent and, therefore, poses a serious threat to the public [1]. Currently, treatment of anthrax relies mainly on antibiotics, but because the initial symptoms are non-specific and the bacteria produces massive amounts of toxins sending the patient into shock, the disease is often beyond treatment once the specific symptomatic stage is reached [2]. Therefore, pre-exposure vaccination is very important in medical countermeasures against anthrax.

The protective antigen is one of three components of the anthrax toxin [3]. Anthrax toxins comprise the following three polypeptide components: the 83 kDa protective antigen (PA); the 90 kDa lethal factor (LF); and the 89 kDa edema factor (EF). The LF and EF components are enzymes that are carried into the cell by an activated form of PA and each require PA in order to exert their toxic effects inside a host cell. During infection, the full 83 kDa length of PA (PA 83) produced from *B. anthracis* binds to expressed receptors on the surface of a host cell [11, 12]. These receptors are commonly known as anthrax toxin receptors (ATRs). Once bound to the ATR, the PA 83 undergoes a cleavage by cell-associated furin-like proteases, which results in the release of a 20 kDa fragment of PA thereby leaving the activated form of PA, the 63 kDa PA fragment (PA 63). The PA 63 fragment is then formed into a heptameric ring, which binds with LF or EF. The PA63:LF or PA63:EF complexes, referred to respectively as lethal toxin (LeTx) and edema toxin (EdTx), are then internalized into the cell following which, the LF and EF components are unbound and released into the cytoplasm [12]. The LF and EF components are thereby allowed to exert their actions on the cell. Thus, various attempts have been made to bind or neutralize PA in order to prevent the above chain of events resulting in LF and EF translocation into the cytoplasm.

PA is the major component of the currently licensed human vaccine for anthrax [4]. The PA-based cell-free subunit anthrax vaccine is highly effective, but the vaccination is burdensome, requiring subcutaneous infections at 0, 2, and 4 weeks and 6, 12, and 18 months with subsequent yearly boosters [5]. Furthermore, not all vaccine recipients mount a protective response. For example, very young children and immuno-compromised persons are often unable to generate effective immune response to vaccination [6].

Post-exposure vaccination is sometimes required for prophylaxis or therapy of BT/BW agent-mediated diseases. However, the use of PA as a post-exposure vaccine may be limited. Since PA is a natural component of anthrax toxin and may contribute to toxin formation, it may not be safe to administer a PA-based vaccine to persons who have been or are suspected of having been exposed to anthrax.

Although the currently available anthrax vaccines are effective, they require a multi-dose schedule. Furthermore, not all vaccine recipients mount a protective response, even after receiving the recommended immunization schedule. In addition, post-exposure vaccination with the PA-based vaccine would be potentially dangerous because it may combine with trace amounts of the other two components of the anthrax toxin, lethal factor (LF) and edema factor (EF) and cause toxicity.

The efficacy of anthrax vaccine correlates with the development of humoral responses to PA exposure. Anti-PA antibodies play a key role in protection against anthrax [7]. It has therefore been postulated that anti-PA antibodies would be a good alternative to vaccines in the prophylaxis and therapy of anthrax. For post-exposure therapy of infectious diseases, passive antibody administration has substantial advantages over the administration of other therapeutic agents, including low toxicity and high specific activity, and an immediate effect compared with vaccines or antibiotics. For pre-exposure vaccination, antibody genes can be delivered in vivo as vaccines [8]. The expressed antibody in vivo was reported to be detectable as early as day 3, to reach peak level at day 7, and to maintain therapeutic level in serum for more than 7 months after a single administration of antibody gene delivery [9, 10]. The attractive feature of antibody gene delivery for vaccination is that the expressed antibodies will exert functions regardless of whether the host has a fully functional immune system.

Various approaches have been taken to obtain monoclonal antibodies (mAbs) directed to anthrax PA. Examples of these approaches are discussed in PCT publications WO/2005/023177 and WO/2007/084107. In this regard, it has been suggested by Mohamed et al (2004) [12] that, in some cases, anti-PA monoclonal antibodies may result in an increased potency of anthrax lethal toxin (LeTx) by increasing the internalization of LF.

Thus, there exists a need for an anti-PA antibody that is effective in neutralizing PA and immunizing the host against anthrax infection.

SUMMARY OF THE INVENTION

In one aspect, the invention provides an isolated monoclonal anti-anthrax protective antigen (anti-PA) antibody, or an antigen-binding fragment thereof, wherein the antibody or the fragment comprises:
  a) a VH chain selected from:
  amino acid sequence SEQ ID NO: 2;
  amino acid sequence SEQ ID NO: 6;
  amino acid sequence encoded by SEQ ID NO: 1; or
  amino acid sequence encoded by SEQ ID NO: 5; and
  b) a VL chain selected from:
  amino acid sequence SEQ ID NO: 4;
  amino acid sequence SEQ ID NO: 8;
  amino acid sequence encoded by SEQ ID NO: 3; or
  amino acid sequence encoded by SEQ ID NO: 7.

In another aspect, the invention provides an isolated monoclonal anti-anthrax protective antigen (anti-PA) antibody wherein the antibody includes a VH chain with complementarity determining regions CDR1, CDR2 and CDR3 wherein:
  the CDR1 region comprises the amino acid sequence SEQ ID NO: 9 or SEQ ID NO: 15;
  the CDR2 region comprises the amino acid sequence SEQ ID NO: 10 or SEQ ID NO: 16; and
  the CDR3 region comprises the amino acid sequence SEQ ID NO: 11 or SEQ ID NO: 17.

In another aspect, the invention provides an isolated monoclonal anti-anthrax protective antigen (anti-PA) antibody wherein the antibody includes a VL chain with complementarity determining regions CDR1, CDR2 and CDR3 wherein:

the CDR1 region comprises the amino acid sequence SEQ ID NO: 12 or SEQ ID NO: 18;
the CDR2 region comprises the amino acid sequence SEQ ID NO: 13 or SEQ ID NO: 19; and
the CDR3 region comprises the amino acid sequence SEQ ID NO: 14 or SEQ ID NO: 20.

In a further aspect, the invention provides hybridomas which produce the antibodies of the invention.

A DNA construct comprising a first nucleotide sequence encoding an antibody VH chain and a second nucleotide sequence encoding an antibody VL chain, wherein the first nucleotide sequence is SEQ ID NO:1 or SEQ ID NO:5 and wherein the second nucleotide sequence is SEQ ID NO:3 or SEQ ID NO:7.

In another aspect, the invention provides vectors incorporating the above mentioned DNA constructs and isolated host cells transfected with such vectors.

In another aspect, the invention provides a pharmaceutical composition containing the antibodies of the invention in combination with a suitable carrier, diluent or excipient.

BRIEF DESCRIPTION OF THE DRAWINGS

One or more embodiments of the invention will now be described by way of example only with reference to the appended drawings wherein.

DETAILED DESCRIPTION OF THE INVENTION

The present invention provides anti-protective antigen (PA) antibodies and uses and therapies based on such antibodies in the treatment and/or diagnosis of anthrax. The invention includes the use of intact antibodies, and preferably monoclonal antibodies, or one or more antigen binding portions or fragments of such antibodies. The antibodies of the invention, or fragments thereof, inhibit or neutralize the function or activity of PA.

Various terms are used in the present description and, unless otherwise indicated, will be assumed to have the following definitions:

As used herein, "protective antigen" and "PA" refer to the protective antigen protein produced by the bacterium *Bacillus anthracis* (anthrax), and include any variants, isoforms and species homologs of anthrax protective antigen, which may be naturally expressed by the bacterium or recombinantly expressed. The terms "protective antigen" and "PA" refer to both the 83 kDa (PA83) and 63 kDa (PA63) forms of anthrax PA, unless a term is specifically limited to one form or the other.

In one aspect, an anti-PA antibody of the invention "neutralizes" an anthrax toxin (i.e., LeTx or EdTx). As used herein, "neutralizes" and grammatical variations thereof, refer to an activity of an antibody of the present invention that prevents entry or translocation of EF or LF into the cytoplasm of a cell susceptible to anthrax infection. The antibody achieves this effect by binding with the anthrax PA. Although not intending to be limited by any particular mechanism of action, binding of an antibody of the invention to anthrax PA can result in prevention of toxin translocation into a cell's cytoplasm at a number of different points during the infection process, e.g., (1) binding of anthrax PA to an anthrax toxin receptor (ATR) on a cell, (2) cleavage of the PA 83 into the activated PA 63 form, (3) formation of a heptamer comprising seven PA 63 units, and (4) binding (or otherwise associating) of the LF or EF to the PA 63 heptamer. An antibody of the invention can neutralize anthrax toxin by inhibiting or blocking any one or more of the different points during the infection process through binding to anthrax PA.

Various in vitro assays will be known to persons skilled in the art for determining whether an antibody (or any other compound) can neutralize a toxin. For example, a toxin neutralization assay (TNA), which will be known to persons skilled in the art and which is discussed further below, may be used.

As used herein, the term "antibody" will be understood to mean an immunoglobulin molecule or a fragment thereof having the ability to specifically bind to a particular antigen. In the context of the present invention the term anti-PA antibody will be understood to comprise an antibody that specifically binds to PA. Further, as used herein, the term "antibody" will be understood has being an anti-PA antibody. The term "antibody" as used herein will also be understood to include whole antibodies as well as antigen binding portions, or fragments thereof retaining antigen binding ability. Such fragments are well known in the art and include Fab, Fab', F(ab')$_2$, Fv, ScFv and Fd fragments.

As will be known to persons skilled in the art, the term "antibody" refers to a glycoprotein comprising at least two heavy (H) chains and two light (L) chains inter-connected by disulfide bonds. Each heavy chain is comprised of a heavy chain variable region (abbreviated herein as VH) and a heavy chain constant region. The heavy chain constant region is comprised of three domains, CH1, CH2 and CH3. Each light chain is comprised of a light chain variable region (abbreviated herein as VL) and a light chain constant region. The light chain constant region is comprised of one domain, CL. The VH and VL regions can be further subdivided into regions of hypervariability, termed complementarily determining regions (CDR), interspersed with regions that are more conserved, termed framework regions (FR). Each VH and VL is composed of three CDRs and four FRs, arranged from the amino-terminus to the carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g. effecter cells) and the first component (Clq) of the classical complement system.

The term "antigen-binding portion" of an antibody (or simply "antibody portion"), as used herein, refers to one or more fragments of an antibody that retain the ability to bind to an antigen (e.g., in the present case, *B. anthracis* PA). As known in the art, the antigen-binding function of an antibody can be performed by fragments of a full-length antibody. As discussed above, the term "binding fragments," which is encompassed within the term "antigen-binding portion" of an antibody, includes (i) a Fab fragment, a monovalent fragment consisting of the VL, VH, CL and CH1 domains; (ii) a F(ab')$_2$ fragment, a bivalent fragment comprising two Fab' fragments linked by a disulfide bridge at the hinge region; (iii) a Fd fragment consisting of the VH and CH1 domains; (iv) a Fv fragment consisting of two non-covalently associated VL and VH domains of a single arm of an antibody, (v) a dAb fragment, which consists of a VH domain; and (vi) an isolated complementarily determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules known as a single chain Fv (scFv). Such single chain antibodies are also intended to be encompassed within the terms "antibody" or "antigen-binding portion of an antibody". These antibody fragments are obtained using conventional techniques known to those with skill in the art, and the fragments are screened for utility in the same manner as are intact antibodies.

The term "epitope" means a protein determinant capable of specific binding to an antibody. Epitopes typically consist of chemically active surface groupings of molecules such as amino acids or sugar side chains and usually have specific three dimensional structural characteristics, as well as specific charge characteristics.

The terms "monoclonal antibody" or "monoclonal antibody composition" as used herein refer to a preparation of antibody molecules of single molecular composition. A monoclonal antibody composition displays a single binding specificity and affinity for a particular epitope.

The term "hybridoma" as used herein refers to cells that have been engineered to produces a desired antibody. In general, hybridomas are formed by extracting B-cells from the spleen of an animal that has been challenged with a particular antigen. The B-cells are fused with myeloma tumour cells to produce a hybridoma.

The term "recombinant antibody", as used herein, is intended to include all antibodies that are prepared, expressed, created or isolated by recombinant means, such as (a) antibodies isolated from an animal (e.g. a mouse), (b) antibodies expressed using a recombinant expression vector transfected into a host cell, and (c) antibodies prepared, expressed, created or isolated by any other means that involves splicing of desired immunoglobulin gene sequences to other DNA sequences. Such recombinant antibodies have variable and constant regions derived from given (e.g. mouse or human) germline immunoglobulin sequences. However, in other embodiments, such recombinant antibodies can be subjected to in vitro mutagenesis or, in some cases, in vivo somatic mutagenesis and thus the amino acid sequences of the VH and VL regions of the recombinant antibodies are sequences that, while derived from and related to a specific germline VH and VL sequences, may not naturally exist.

As used herein the term "vector" may be any number of nucleic acids into which a desired sequence may be inserted by restriction and ligation for transport between different genetic environments or for expression in a host cell. Vectors are typically composed of DNA although RNA vectors are also available. Vectors include but are not limited to plasmids and phagemids. A cloning vector is one which is able to replicate in a host cell and which is further characterized by one or more endonuclease restriction sites at which the vector may cut in a determinable fashion and into which a desired DNA sequence may be ligated such that the new recombinant vector retains its ability to replicate in the host cell. The vectors may be constructed in such a way as to enable the inserted DNA sequence to be operably linked or joined to specific regulatory sequences and may therefore be expressed as an RNA transcript. Such vectors are referred to as "recombinant expression vectors" or "expression vectors".

The term "recombinant host cell" or "host cell" is used herein to refer to a cell into which a recombinant expression vector has been introduced and the progeny of such cell.

As discussed further below, according to one aspect of the present invention, two novel antibodies, designated herein as 13E3 and 3E1, have been isolated by challenging BALB/c mice with PA and subsequently obtaining splenocytes therefrom. The spelnocytes were fused with various myeloma cells from which the 13E3 and 3E1 hybridomas were isolated. These hybridomas were then analysed for immunoreactivity to PA using a toxin neutralization assay (TNA). A method for generating the hybridomas of the invention is described below. However, various other methods will be known to persons skilled in the art.

The hybridomas 13E3 and 3E1 of the present invention have been deposited with the International Depositary Authority of Canada (IDAC) (National Microbiology Laboratory, Public Health Agency of Canada, 1015 Arlington Street, Winnipeg, Manitoba, Canada R3E 3R2) on Jul. 23, 2008 and have received accession numbers 230708-02 and 230708-01, respectively.

The DNA sequences of the VH and VL chains of the antibodies 13E3 and 3E1 were determined and their respective amino acid sequences deduced. The DNA sequences of the VH and VL chains of the antibody 13E3 have been identified herein to be as follows:

```
VH DNA sequence of 13E3:
                                                (SEQ ID NO: 1)
5'-CAGGTCAAGCTGCAGGAGTCTGGAGCTGAGCTGGTGAGGCCTGGGGC
TTCAGTGAAGCTGTCCTGCAAGACTTCTGGATACATCTTCACCAACTACT
GGATTCACTGGGTAAAACAGAGGTCTGGACAGGGCCTTGAGCGGATTGCA
AGGATTTATCCTGGAACTGGTGGTACTTACTACAATGAGAAGTTCAAGGG
CAAGGCCACACTGACTGCAGACAAATCCTCCAGCACTGCCTACATGCAGC
TCAGCAGCCTGAAATCTGAGGACTCTGCTGTCTATTTCTGTGCAAGATGG
GATCTACATTTCTCTATGGACTACTGGGGCCAAGGGACCACGGTCACCGT
CTCCTCA-3'.

VL DNA sequence of 13E3:
                                                (SEQ ID NO: 3)
5'-CAAATTGTTCTCACCCAGTCTCCAGCAATCATGTCTGCATCTCCAGG
GGAGAAGGTCACCATGACCTGCAGTGCCAGTTCAAGTGTACGTTACATGC
ACTGGTACCAGCAGAAGTCGGGCACCTCCCCCAAAAGATGGATTTATGAC
ACATCCAAACTGGCTTCTGGAGTCCCTGCTCGCTTCAGTGGCAGTGGGTC
TGGGACCTCTTACTCTCTCACAATCAGCAGCATGGAGGCTGAAGATGCTG
CCACTTATTACTGCCAGCAGTGGAGTGGTAACCCGCTCACGTTCGGTGCT
GGGACCAAGCTGGAAATAAAACGG-3'.
```

The deduced amino acid sequences of the VH and VL chains of the antibody 13E3 have been herein identified to be as follows:

```
VH deduced amino acid sequence of 13E3:
                                                (SEQ ID NO: 2)
NH2-QVKLQESGAELVRPGASVKLSCKTSGYIFTNYWIHWVKQRSGQGLE
RIARIYPGTGGTYYNEKFKGKATLTADKSSSTAYMQLSSLKSEDSAVYFC
ARWDLHFSMDYWGQGTTVTVSS-COOH.

VL deduced amino acid sequence of 13E3:
                                                (SEQ ID NO: 4)
N2H-QIVLTQSPAIMSASPGEKVTMTCSASSSVRYMHWYQQKSGTSPKRW
IYDTSKLASGVPARFSGSGSGTSYSLTISSMEAEDAATYYCQQWSGNPLT
FGAGTKLEIKR-COOH.
```

The DNA sequences of the VH and VL chains of the antibody 3E1 have been identified herein to be as follows:

```
VH DNA sequence of 3E1:
                                                (SEQ ID NO: 5)
5'-GAGGTGAAGCTGCAGGAGTCWGGAGGAGGCTTGGTGCAACCTGGAGG
ATCCATGAAACTCTCTTGTGCTGCCTCTGGATTCAGTTTTAGTGACGCCT
GGATGGACTGGGTCCGCCAGTCTCCAGAGAAGGGCCTTGAGTGGGTTGCT
GAAATTAGAAGCAAAGCTAAGAATCATGCAACATTCTATGCTGAGTCTGT
GAAAGGGAGGTTCACCATCTCAAGAGATGATTCCAAAAGTAGTGTCTACC
TGCAAATGAACAGCTTAAGAGGTGAAGACACTGGCATTTATTACTGCACC
GCTGGGACGGGCGTCTGGGGCCAAGGGACCACGGTCACCGTCTCCTC
A-3'.
```

-continued

VL DNA sequence of 3E1:

(SEQ ID NO: 7)
5'-GACATCCAGATGACVCAGTCTCCACTCACTTTGTCGGTTACCTTTGG
ACAACCAGCCTCCATCTCTTGCAAGTCAAGTCAGAGCCTCTTAGCTAGTG
ATGGAGAGACATATTTGAATTGGTTGTTACAGAGGCCAGACCAGTCTCTA
AAGCGCCTAATCTATCTGGTGTCTAAACTGGACTCTGGAGTCCCTGACAG
GTTCACTGGCAGTGGATCAGGGACAGATTTCACACTGAAAATCAGCAGAG
TGGAGGCTGAGGATTTGGGAGTTTATTATTGTTGGCAAGGTACACATTTT
CCTCAGACGTTCGGTGGAGGCACCGAGCTGGAATTCAAACGG-3'.

The deduced amino acid sequences of the VH and VL chains of the antibody 3E1 have been identified herein to be as follows: herein as SEQ ID NOs: 6 and 8, respectively.

VH deduced amino acid sequence of 3E1:

(SEQ ID NO: 6)
N2H-EVKLQESGGGLVQPGGSMKLSCAASGFSFSDAWMDWVRQSPEKGLE
WVAEIRSKAKNHATFYAESVKGRFTISRDDSKSSVYLQMNSLRGEDTGIY
YCTAGTGVWGQGTTVTVSS-COOH.

VL deduced amino acid sequence of 3E1:

(SEQ ID NO: 8)
N2H-DIQMTQSPLTLSVTFGQPASISCKSSQSLLASDGETYLNWLLQRPD
QSLKRLIYLVSKLDSGVPDRFTGSGSGTDFTLKISRVEAEDLGVYYCWQG
THFPQTFGGGTELEFKR-COOH.

In addition, the complementarity determining regions (CDRs) of the above mentioned VH and VL chains have been identified herein to have the following amino acid sequences:

```
CDRs of Antibody 13E3:
13E3 VH CDR1: NYWIH.              (SEQ ID NO: 9)

13E3 VH CDR2: RIYPGTGGTYYNEKFKG.  (SEQ ID NO: 10)

13E3 VH CDR3: WDLHFSMDY.          (SEQ ID NO: 11)

13E3 VL ODR1: SASSSVRYMH.         (SEQ ID NO: 12)

13E3 VL CDR2: DTSKLAS.            (SEQ ID NO: 13)

13E3 VL CDR3: QQWSGNPLT.          (SEQ ID NO: 14)

CDRs of Antibody 3E1:
3E1 VH CDR1:  DAWMD.              (SEQ ID NO: 15)

3E1 VH CDR2:  EIRSKAKNHATFYAESVKG. (SEQ ID NO: 16)

3E1 VH CDR3:  GTGV.               (SEQ ID NO: 17)

3E1 VL ODR1:  KSSQSLLASDGETYLN.   (SEQ ID NO: 18)

3E1 VL CDR2:  LVSKLDS.            (SEQ ID NO: 19)

3E1 VL CDR3:  WQGTHFPQT.          (SEQ ID NO: 20)
```

Although the above mentioned sequences are disclosed herein, it will be understood that the invention will include other nucleotide and amino acid sequences that deviate from the specific sequences disclosed while still retaining the same functional characteristics. Thus, SEQ ID NOs: 1 to 20, and any other sequences disclosed herein, will be understood to include "conservative sequence modifications", that is, nucleotide and amino acid sequence modifications that do not significantly affect or alter the binding characteristics of the respective antibody encoded by a given nucleotide or amino acid sequence. Such modifications will include substitutions, insertions and/or deletions. Various such modifications will be known to persons skilled in the art.

Thus, in one aspect, the invention provides novel anti-PA monoclonal antibodies that neutralize *B. anthracis* PA. In particular, the invention provides two anti-PA monoclonal antibodies identified as 13E3 and 3E1. It will be understood that fragments of such antibodies including the respective antigen binding portions are encompassed within the scope of the present invention. In another aspect, the invention provides at least two hybridomas, namely, 13E3 and 3E1, that produce the monoclonal antibodies of the invention.

In a further aspect, the invention provides recombinant antibodies having the antigen binding characteristics (i.e. PA neutralizing ability) of the antibodies 13E3 and 3E1 of the present invention. In particular, the invention provides recombinant antibodies encoded by nucleotide sequences of the VH and VL chains for 13E3 and 3E1 discussed above. That is, the recombinant antibodies of the invention comprise the VH and VL chains of the antibodies 13E3 or 3E1 or functional equivalents thereof. Various methods for producing such recombinant antibodies will be known to persons skilled in the art. In one embodiment, for example, the nucleotide sequences for the VH and VL chains of antibodies 13E3 and 3E1 may be incorporated within a vector and then introduced into a host cell by transfection. The host cell may then be used to produce antibodies having the desired VH and VL chains or antigen-binding fragments thereof.

In another aspect, the invention provides Fv fragments of the antibodies of the invention. That is, the invention provides Fv fragments comprising the VH and VL amino acid sequences discussed above. For example, a Fv fragment according to the invention would include a VH chain selected from SEQ ID NOs: 2 and 6 or encoded by the nucleotide sequence selected from SEQ ID NOs: 1 and 5. Similarly, a Fv fragment according to the invention would include a VL chain selected from SEQ ID NOs: 4 and 8 or encoded by the nucleotide sequence selected from SEQ ID NOs: 3 and 7.

In another aspect, the invention provides scFv fragments encoded by a nucleotide sequence combining the sequences for the VH and VL chains discussed above. More specifically, the invention provides in one aspect an scFv fragment encoded by a nucleotide sequence comprising one of SEQ ID NOs: 1 and 5 (the VH chains) and one of SEQ ID NOs: 3 and 7 (the VL chains).

In another aspect, the invention provides humanized antibodies comprising the antigen binding regions of the antibodies 13E3 and 3E1 described herein.

In another aspect, the invention encompasses pharmaceutical compositions comprising the antibodies or antibody fragments discussed above in combination with one or more carriers, diluents excipients etc. Also within the context of the present invention are methods of using such compositions in the prophylaxis, treatment or diagnosis of anthrax infections. As will be understood, in one embodiment, a composition containing one or more of the antibodies and/or fragments, can be administered to a mammal to immunize the mammal against anthrax.

In a further embodiment, the antibodies of the present invention can be labelled using methods known in the art and be used to detect the presence of PA in a sample.

Aspects of the present invention will be illustrated by means of the following examples. It will be understood that the following examples are not intended to limit the scope of the invention in any way.

EXAMPLE 1

Preparation of Anti-PA Monoclonal Antibodies

Materials and Methods
Immunization—PA Challenge of Mice
Female BALB/c mice were obtained from the pathogen-free mouse breeding colony at Defence Research and Development Canada (DRDC)-Suffield with the original breeding pairs purchased from Charles River Canada (St Constant, QC). The use of these mice was reviewed and approved by the Animal Care Committee at DRDC-Suffield. Care and handling of the mice followed the guidelines set out by the Canadian Council on Animal Care. Mice (6-8 weeks old) were intraperitoneally immunized with 100 µl of protective antigen (PA)-based anthrax vaccine, designated "anthrax vaccine adsorbed" (AVA) emulsified in 100 µl of TiterMax™ Gold adjuvant (Sigma-Aldrich, Oakville, ON). Booster immunizations were carried out every other week with the same dose of AVA emulsified in TiterMax Gold adjuvant. The mice were bled from the tail vein, and the anti-PA antibody titers were checked by an enzyme-linked immunosorbent assay (ELISA) (as described below).

Cell Fusion—Preparation of Hybridomas

Spleens were aseptically dissected from the immunized mice three days after the last booster and were ground gently with autoclaved frosted-glass slides in Dulbecco's Modified Eagle's Medium (DMEM) (Invitrogen, Burlington, ON) and then filtered through a wire mesh screen to prepare splenocytes. Hybridomas were produced by fusing the splenocytes with Sp 2/0 myeloma cells obtained from American Type Culture Collection (ATCC, Manassas, Va.) using a Clonacell-HY™ Kit (StemCell Technologies, Vancouver, BC) following the manufacturer's instructions. After 2 weeks in semi-solid medium, single hybridoma clones were picked and transferred to 96-well tissue culture plates (Costar, Corning, N.Y.) and grown for 3-4 days in Clonacell™ Medium E. Hybridoma supernatants were screened for anti-PA monoclonal antibody (mAb) production by ELISA (as described below).

ELISA

Detection of anti-PA antibodies in the immune sera from AVA-immunized mice to evaluate anti-PA immune responses and in the culture supernatants from hybridoma-containing wells to screen anti-PA hybridoma clones were performed by ELISA as follows. Ninety six-well ELISA plates (Nunc maxisorp, Canadian Life Technologies, Burlington, ON) were coated overnight at 4° C. with the recombinant PA at 10 µg/ml in carbonate bicarbonate buffer, pH 9.6. After blocking, the plates were incubated with 100 µl of serum dilutions or culture supernatants for 2 hours at room temperature. Anti-PA antibodies were detected by incubation with 1:3000 diluted HRP-goat anti-mouse IgG (Caltag Laboratories, Burlingame, Calif.) followed by the addition of a tetramethylbenzidine peroxidase substrate (Kirkegaard and Perry Laboratories, Gathersburg, Md.). Absorbance was measured at 635 nm by a microplate autoreader (Molecular Devices, Sunnyvale, Calif.).

Production and Purification of mAbs

All the hybridoma clones secreting anti-PA mAbs were cultured in DMEM supplemented with 10% fetal bovine serum (FBS) initially and then were adapted gradually to and finally expanded in hybridoma serum-free-medium (SFM) (Invitrogen). The anti-PA mAbs were purified from supernatants by a Melon™ gel monoclonal IgG purification kit (Pierce Biotechnology Inc, Rockford, Ill.).

Characterization of mAbs

The immunoreactivities of the purified anti-PA mAbs were analyzed by ELISA, using a process similar to that described above except that the plates were incubated for 2 hours at 37° C. with various concentrations of 0.001-100 µg/ml anti-PA mAbs.

B. anthracis lethal toxin neutralization activity of the anti-PA mAbs were measured by using a colorimetric toxin neutralization assay (TNA). In brief, toxin sensitive mouse macrophage cells (ATCC J774A.1) were seeded at $10^5$ cells per ml into the wells of a 96-well culture plate, and grown overnight in DMEM with 10% FBS at 37° C. in 5% $CO_2$. The culture supernatant was removed from each well in the 96-well plate. In a separate 96-well ELISA plate, twofold dilutions of 13E3 and 3E1 mAbs and a positive neutralizing anti-PA mAb were combined with 2.0 µg/ml of PA and 1.0 µg/ml of lethal factor (LF). After one hour incubation at 37° C., the mAb/lethal toxin (LeTx) mixtures were then added to the cell monolayers in 96-well plate and then incubated at 37° C. for 2 hours. One hundred µl of fresh growth medium and 40 µl of CellTiter™ 96 Aqueous One Solution Cell Proliferation Assay Medium (Promega, Madsion, Wis.) were added. The cells were incubated for a further 2-2.5 hours at 37° C. to allow for color development, and the plate was then scanned in a microplate autoreader at 492 nm. The lowest mAb dilution that resulted in a 492 nm reading equal to 80% or greater of the no-toxin control was used to determine the neutralizing titer.

Isotype Determination

Anti-PA mAbs were isotyped using a mouse IsoStrip™ Kit from Roche Diagnostics (Laval, QC) following the manufacturer's instructions.

Cloning of Heavy and Light Chain Variable Region (VH and VL) of Anti-PA mAbs

Messenger RNAs from the 13E3 and 3E1 hybridoma cells were isolated using the mRNA Quickprep™ kit from Amersham Pharmacia Biotech (Baie d'Urfe, QC). Two µg of mRNA was used as a template for the reverse transcription. cDNAs encoding VH and VL were then amplified by PCR using a set of primers included in the Mouse Single Chain Fragment Variable Module/Recombinant Phage Antibody System (Amersham Pharmacia Biotech). Subsequently, amplified DNAs of VH and VL (350 bp) were further cloned into pCR4blunt-TOPO™ (Invitrogen) vector for DNA sequencing. The associated T3 primer was used for VH or VL DNA sequencing. The sequencing reactions were performed using CEQ™ DTCS Quick Start™ Kit (Beckman Coulter Mississauga, ON). The reaction products were purified by Centri-Sep™ columns (Princeton Separations, Adelphia, N.J.), and then run on an on a CEQ™ 8000 Genetic Analysis System (Beckman Coulter). Sequences were assembled and analyzed using Lasegene™ DNA software (DNA star, Madison, Wis.). The determined DNA sequences and deduced amino acid sequences of the VH and VL chains of the antibodies produced by the hybridomas 13E3 and 3E1 have been described above with reference to SEQ ID NOs: 1 to 8.

Results

Generation of Anti-PA mAbs

BALB/c mice were immunized with AVA. Following the last booster, mice were sacrificed and splenocytes were prepared and fused with myeloma cells in a standard hybridoma fusion protocol. After growth in semisolid medium, hybridoma clones were transferred to individual wells of 96-well plates and cultured, and supernatants were screened for specific reactivity with the PA. A panel of hybridoma clones with specific reactivity for the PA was identified by ELISA and expanded.

Production, Purification and Characterization of Anti-PA mAbs

Figure 1:
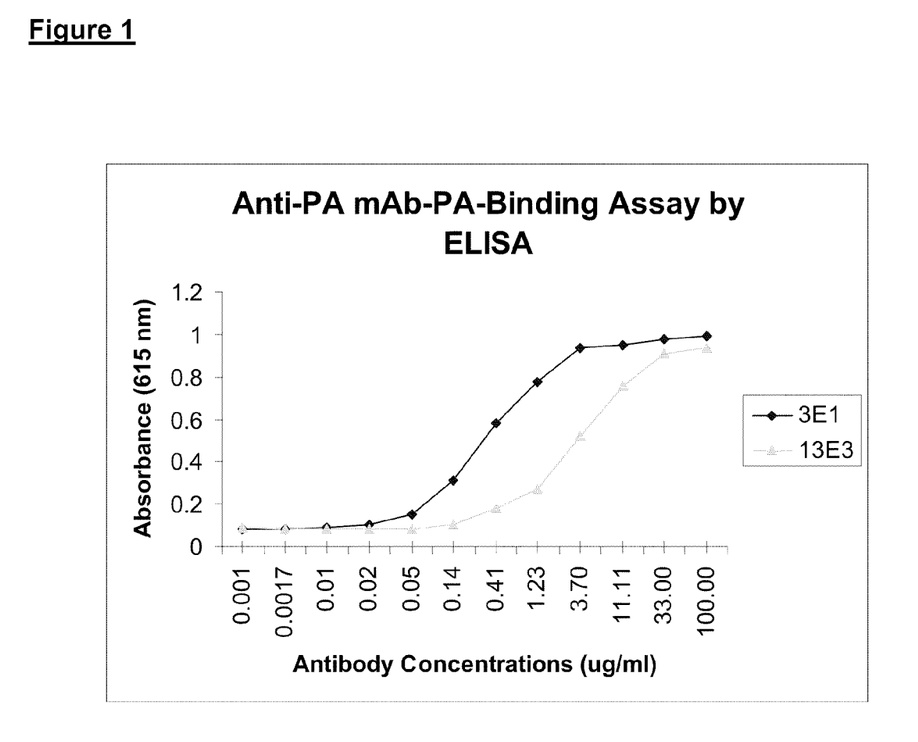
FIG. 1 illustrates the results from an anti-PA mAb binding assay (ELISA).
Figure 2:
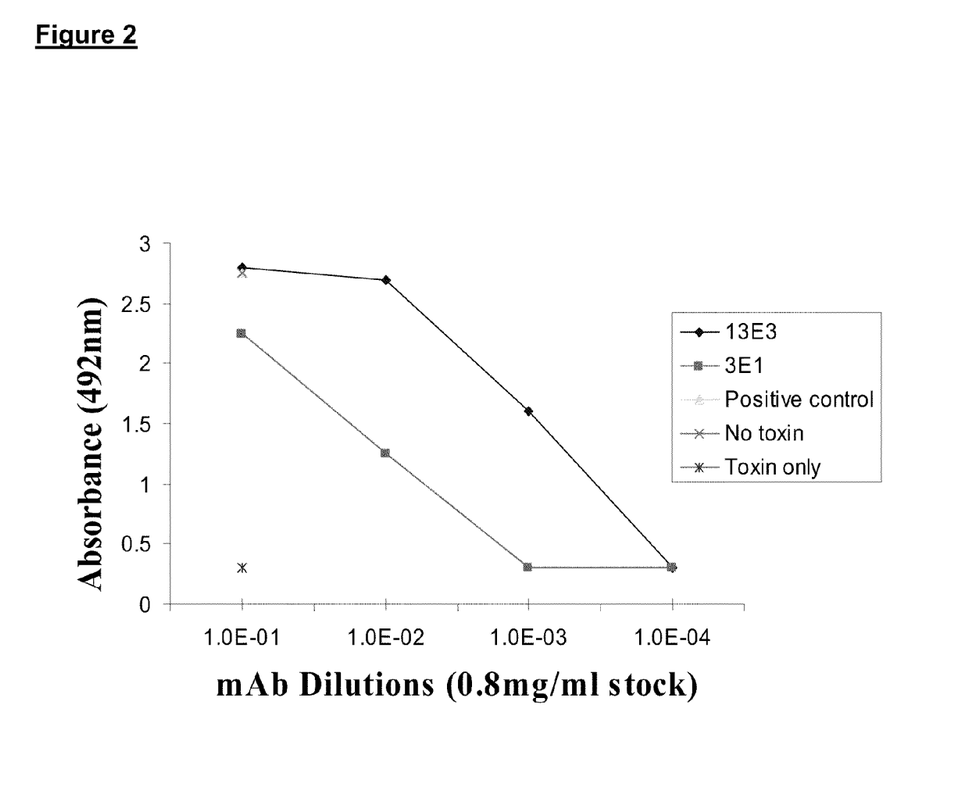
FIG. 2 illustrates the results from an anti-PA neutralization activity assay (TNA).

The hybridoma clones were respectively cultured in DMEM supplemented with 10% FBS initially and then adapted into hybridoma serum free medium (SFM). The mAbs were purified from supernatants by Melon affinity chromatography. The purified mAbs were isotyped using a mouse IsoStrip™ Kit. The 13E3 and 3E1 mAbs showed the same subtype of heavy chain, gamma 1, and the same type of light chain, kappa. The immunoreactivities of the two mAbs to the PA were investigated by ELISA. The two mAbs bound to the PA in a dose-dependent manner (see FIG. 1) and exhibited neutralizing titers of 0.8 µg/ml for 3E1 and 13E3 (see FIG. 2).

As shown in the results described above and illustrated in the figures attached hereto, the antibodies 13E3 and 3E1 (i.e. the antibodies produced by the hybridomas 13E3 and 3E1 of the invention) were found to have the desired anti-PA activity. That is, the antibodies were found to adequately neutralize anthrax PA.

Although the invention has been described with reference to certain specific embodiments, various modifications thereof will be apparent to those skilled in the art without departing from the spirit and scope of the invention as outlined in the claims appended hereto.

References

The following references are cited in the above disclosure. The entire contents of the following references are incorporated herein by reference.

1. Centers of Disease Control and Prevention. www.bt.cdc.gov/agent/anthrax/needtoknow.asp (accessed April 2007)
2. Dixon T C, Meselson M, Guillemin J, Hanna P C. Anthrax. N Engl J Med. 1999 Sep. 9; 341(11):815-26.
3. Blaustein R O, Koehler T M, Collier R J, Finkelstein A. Anthrax toxin: channel-forming activity of protective antigen in plannar phospholipid bilayrers. Proc Natl Acad Sci USA., 1989 April; 86(7):2209-13.
4. Turnbull P C. Anthrax vaccines: past, present and future. Vaccine. 1991 August; 9(8):533-9.
5. Ales N C, Katial R K. Vaccines against biologic agents: users and developments. Respir Care Clin N AM. 2004 March; 10(1):123-46.
6. Pirofski L A, Casadevall A. Use of licensed vaccines for active immunization of the immunocompromised host. Clin Microbiol Rev 1998 January; 11(1):1-26.
7. Pitt M L, Little S F, Ivins B E, Fellows P, Barth J. Hewetson J, Gibbs P, Dertzbaugh M, Friedlander A M. In vitro correlate of immunity in a rabbit model of inhalational anthrax. Vaccine. 2001 Sep. 14; 19(32):4768-73.
8. Lorenzen N, Cupit P M, Einer-Jensen K. Lorenzen E, Ahrens P, Secombes C J, Cunningham C. Immunoprophylaxis in fish by injection of mouse antibody genes. Nat. Biotechnol. 2000 November; 18(11):1177-80.
9. Jiang M, Shi W, Zhang Q, Wang X, Guo M, Cui Z, Su C, Yang Q, Li Y, Sham J, Liu X, Wu M, Qian Q. Gene thereapy using adenovirus-mediates full-length anti-HER-2 antibody for HER-2 overexpression cancers, Clin Cancer Res. 2006 Oct. 15; 12(20 pt1):6179-85.
10. Tjelle T E, Corthay A, Lunde E, Sandlie I, Michaelsen T E, Mathiesen I, Bogen B. Monoclonal antibodies produced by muscle after plasmid injection electroporation. Mol Ther. 2004 March; 9(3):328-36.
11. Bradley, K. A. et al. Identification of the Cellular Receptor for Anthrax Toxin. 2001. Nature 414:225-229.
12. Mohamed, N. et al. Enhancement of Anthrax Lethal Toxin Cytotoxicity: a Subset of Monoclonal Antibodies Against Protective Antigen Increases Lethal Toxin-Mediated Killing of Murine Macrophages. 2004. Infec. And Imm. 72: 3276-3283.

What is claimed is:

1. An isolated monoclonal anti-anthrax protective antigen (anti-PA) antibody, or an antigen-binding fragment thereof, wherein said antibody or said fragment comprises:

a VH chain comprising the amino acid sequence set forth in SEQ ID NO: 2 and a VL chain comprising the amino acid sequence set forth in SEQ ID NO: 4; or a VH chain comprising the amino acid sequence encoded by the nucleic acid sequence set forth in SEQ ID NO: 1 and a VL chain comprising the amino acid sequence encoded by the nucleic acid sequence set forth in SEQ ID NO: 3; or a VH chain comprising the amino acid sequence set forth in SEQ ID NO: 6 and a VL chain comprising the amino acid sequence set forth in SEQ ID NO: 8; or a VH chain comprising the amino acid sequence encoded by the nucleic acid sequence set forth in SEQ ID NO: 5 and a VL chain comprising the amino acid sequence encoded by the nucleic acid sequence set forth in SEQ ID NO: 7.

2. The antibody of claim 1, wherein the antibody includes a VH chain with complementarity determining regions CDR1, CDR2 and CDR3, wherein:

the CDR1 region comprises the amino acid sequence set forth in SEQ ID NO: 9 or SEQ ID NO: 15;

the CDR2 region comprises the amino acid sequence set forth in SEQ ID NO: 10 or SEQ ID NO: 16; and the CDR3 region comprises the amino acid sequence set forth in SEQ ID NO: 11 or SEQ ID NO: 17.

3. The antibody of claim 1, wherein the antibody includes a VL chain with complementarity determining regions CDR1, CDR2 and CDR3, wherein:

the CDR1 region comprises the amino acid sequence set forth in SEQ ID NO: 12 or SEQ ID NO: 18;

the CDR2 region comprises the amino acid sequence set forth in SEQ ID NO: 13 or SEQ ID NO: 19; and the CDR3 region comprises the amino acid sequence set forth in SEQ ID NO: 14 or SEQ ID NO: 20.

4. A hybridoma that produces the antibody according to claim 1.

5. The hybridoma of claim 4, wherein said hybridoma is hybridoma 13E3, having IDAC accession number 230708-02, or hybridoma 3E1, having IDAC accession number 230708-01.

6. The isolated antigen binding fragment according to claim 1, wherein said fragment is a Fv fragment, a single chain Fv fragment, or a Fab fragment.

7. A pharmaceutical composition comprising the monoclonal antibody or the antigen-binding fragment according to claim 1 and a pharmaceutically acceptable carrier, diluent or excipient.

8. A method of immunizing a mammal against anthrax infection comprising administering the pharmaceutical composition of claim 7.

* * * * *